US008733178B2

(12) United States Patent
Bivans et al.

(10) Patent No.: US 8,733,178 B2
(45) Date of Patent: May 27, 2014

(54) PRESSURE SENSING ASSEMBLY AND METHOD FOR AN INFUSION PUMP

(75) Inventors: Matthew Bivans, Middleport, NY (US); Kenneth Corwin, Rochester, NY (US); Troy P. Lindke, Gasport, NY (US); Michael Hungerford, Medina, NY (US); Scott C. Ofslager, Albion, NY (US); Jason Maine, Hamlin, NY (US)

(73) Assignees: Baxter Healthcare S.A., Glattpark (Opfikon) (CH); Baxter International Inc., Deerfield, IL (US)

( * ) Notice: Subject to any disclaimer, the term of this patent is extended or adjusted under 35 U.S.C. 154(b) by 288 days.

(21) Appl. No.: 13/364,007

(22) Filed: Feb. 1, 2012

(65) Prior Publication Data

US 2013/0192380 A1     Aug. 1, 2013

(51) Int. Cl.
*G01B 7/16*     (2006.01)

(52) U.S. Cl.
USPC ............................................... 73/781; 73/169

(58) Field of Classification Search
USPC ........................................... 73/169, 700, 781
See application file for complete search history.

(56) References Cited

U.S. PATENT DOCUMENTS

| | | | |
|---|---|---|---|
| 3,955,901 A | 5/1976 | Hamilton | |
| 4,856,339 A * | 8/1989 | Williams | 73/714 |
| 5,419,684 A * | 5/1995 | Struble et al. | 417/44.2 |
| 5,591,344 A | 1/1997 | Kenley et al. | |
| 5,630,935 A | 5/1997 | Treu | |
| 5,645,734 A | 7/1997 | Kenley et al. | |
| 5,651,893 A | 7/1997 | Kenley et al. | |
| 5,658,456 A | 8/1997 | Kenley et al. | |
| 5,670,050 A | 9/1997 | Brose et al. | |
| 5,674,390 A | 10/1997 | Matthews et al. | |
| 5,674,397 A | 10/1997 | Pawlak et al. | |
| 5,674,404 A | 10/1997 | Kenley et al. | |
| 5,690,821 A | 11/1997 | Kenley et al. | |
| 5,690,831 A | 11/1997 | Kenley et al. | |
| 5,702,606 A | 12/1997 | Peter, Jr. et al. | |
| 5,705,066 A | 1/1998 | Treu et al. | |
| 5,707,086 A | 1/1998 | Treu et al. | |
| 5,714,060 A | 2/1998 | Kenley et al. | |
| 5,716,531 A | 2/1998 | Kenley et al. | |
| 5,725,776 A | 3/1998 | Kenley et al. | |
| 5,762,782 A | 6/1998 | Kenley et al. | |
| 5,783,072 A | 7/1998 | Kenley et al. | |
| 5,842,841 A | 12/1998 | Danby et al. | |
| 5,863,421 A | 1/1999 | Peter et al. | |
| 6,204,771 B1 | 3/2001 | Ceney | |
| 6,213,738 B1 | 4/2001 | Danby et al. | |
| 6,347,553 B1 * | 2/2002 | Morris et al. | 73/781 |
| 6,412,350 B1 | 7/2002 | Swift | |
| 6,629,934 B2 * | 10/2003 | Mault et al. | 600/538 |
| 6,852,094 B2 * | 2/2005 | Beck et al. | 604/67 |
| 6,905,314 B2 * | 6/2005 | Danby | 417/53 |
| 7,201,059 B2 | 4/2007 | Lin et al. | |
| 2011/0314927 A1 | 12/2011 | Lopez, III | |

* cited by examiner

*Primary Examiner* — Max Noori
(74) *Attorney, Agent, or Firm* — Greer, Burns & Crain, Ltd.

(57) ABSTRACT

A pressure sensing assembly for an infusion pump, including: a tubing guide arranged to receive tubing; a displaceable load assembly at least partially disposed within the tubing guide and with a first surface facing in a first direction; a load cell facing the load assembly in the first direction; and a displacement assembly engaged with the tubing guide, facing the first surface in a second direction, opposite the first direction, and exerting a first force on the load assembly in the first direction. The load cell is arranged to detect a second force, greater than the first force, acting on the load cell in the second direction.

24 Claims, 6 Drawing Sheets

PRESSURE SENSING ASSEMBLY AND METHOD FOR AN INFUSION PUMP

TECHNICAL FIELD

The present disclosure relates to a pressure sensing assembly and method for an infusion pump, in particular, an assembly and method using force to draw a load plate away from a load cell.

BACKGROUND

U.S. Pat. No. 6,347,553 teaches the use of a resilient material, placed between a metal housing of an infusion pump and a load plate of a load sensing system, to exert a force, in a first direction, on a surface of the load plate facing in a second opposite direction toward a load cell for the load sensing system. In response to a load exerted on the load plate in the second direction, for example, by tubing in the infusion pump, the load plate displaces in the second direction compressing the resilient material. When the load is removed, the resilient material "rebounds" to displace the load plate in the first direction.

SUMMARY

According to aspects illustrated herein, there is provided a pressure sensing assembly for an infusion pump, including: a tubing guide arranged to receive tubing; a displaceable load assembly at least partially disposed within the tubing guide and with at least one first surface facing in a first direction; a load cell facing the load assembly in the first direction; and a displacement assembly engaged with the tubing guide, facing the at least one first surface in a second direction, opposite the first direction, and exerting a first force on the load assembly in the first direction. The load cell is arranged to detect a second force, greater than the first force, acting on the load cell in the second direction.

According to aspects illustrated herein, there is provided a pressure sensing assembly for an infusion pump, including: a tubing guide with at least one slot; tubing including a longitudinal axis and at least a portion disposed in the at least one slot; a displaceable load assembly at least partially disposed within the tubing guide and with a first surface in contact with the tubing; a load cell facing the longitudinal axis in a first direction; and a displacement assembly facing at least a portion of the load assembly in a second direction, opposite the first direction, and exerting a first force on the load assembly in the first direction. In response to a second force, greater than the first force, on the first surface, the load assembly is arranged to displace in the second direction. The load cell is arranged to detect the second force.

According to aspects illustrated herein, there is provided a pressure sensing assembly for an infusion pump, including: a tubing guide arranged to receive tubing; a displaceable load assembly at least partially disposed within the tubing guide and including a load plate arranged to contact the tubing, and an attraction plate fixed to the load plate and including a magnetic material. The pressure sensing assembly includes: a load cell; and a plurality of magnets, fixedly secured to the tubing guide and urging: at least a portion of the attraction plate toward the tubing guide with a first force; and the load plate away from the load cell. The load cell is arranged to detect a second force, greater than the first force, acting on the load plate counter to the first force.

According to aspects illustrated herein, there is provided a pressure sensing assembly for an infusion pump, including: a tubing guide arranged to receive tubing; a displaceable load assembly at least partially disposed within the tubing guide; a load cell; and a displacement assembly engaged with the tubing guide and exerting a first force on the load assembly. The first force draws at least a portion of the load assembly toward the tubing guide. The load cell is arranged to detect a second force, greater than the first force, acting on the load assembly counter to the first force.

According to aspects illustrated herein, there is provided a method of measuring pressure in tubing for an infusion pump using a pressure sensing assembly including: tubing; a tubing guide; a displaceable load assembly with at least one first surface facing in a first direction; a load cell facing the load assembly in the first direction; and a displacement assembly engaged with the tubing guide. The method includes: disposing at least a portion of the tubing in the tubing guide; exerting, using the displacement assembly, a first force on the load assembly; drawing at least a portion of the load assembly toward the tubing guide with the first force; and detecting a second force, greater than the first force, acting on the load assembly counter to the first force.

According to aspects illustrated herein, there is provided a method of measuring pressure in tubing for an infusion pump using a pressure sensing assembly including: tubing; a tubing guide with at least one slot; tubing including a longitudinal axis; a displaceable load assembly; a load cell facing the longitudinal axis in a first direction; and a displacement assembly facing at least a portion of the load assembly in a second direction, opposite the first direction. The method includes: disposing at least a portion of the tubing in the at least one slot; contacting a first surface of the load assembly with the tubing; exerting, using the displacement assembly, a first force on the load assembly in the first direction; displacing the load assembly, in response to a second force, greater than the first force, on the first surface, in the second direction; and detecting, using the load cell, the second force.

According to aspects illustrated herein, there is provided a method of measuring pressure in tubing for an infusion pump using a pressure sensing assembly including: tubing; a tubing guide; a displaceable load assembly at least partially disposed within the tubing guide and including: a load plate arranged to contact the tubing and an attraction plate fixed to the load plate and including a magnetic material; a load cell; and a plurality of magnets, fixedly secured to the tubing guide. The method includes: disposing at least a portion of the tubing in the tubing guide; generating a first force using the plurality of magnets; drawing, with the first force: at least a portion of the attraction plate toward the tubing guide; and the load plate away from the load cell; and detecting, using the load cell, a second force, greater than the first force, acting on the load plate counter to the first force.

According to aspects illustrated herein, there is provided a method of measuring pressure in tubing for an infusion pump using a pressure sensing assembly including: tubing; a tubing guide; a displaceable load assembly at least partially disposed within the tubing guide; a load cell; and a displacement assembly engaged with the tubing guide. The method includes: displacing at least a portion of the tubing in the tubing guide; generating a first force with the displacement assembly; drawing, using the first force, at least a portion of the load assembly toward the tubing guide; and detecting, using the load cell, a second force, greater than the first force, acting on the load assembly counter to the first force.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 1:
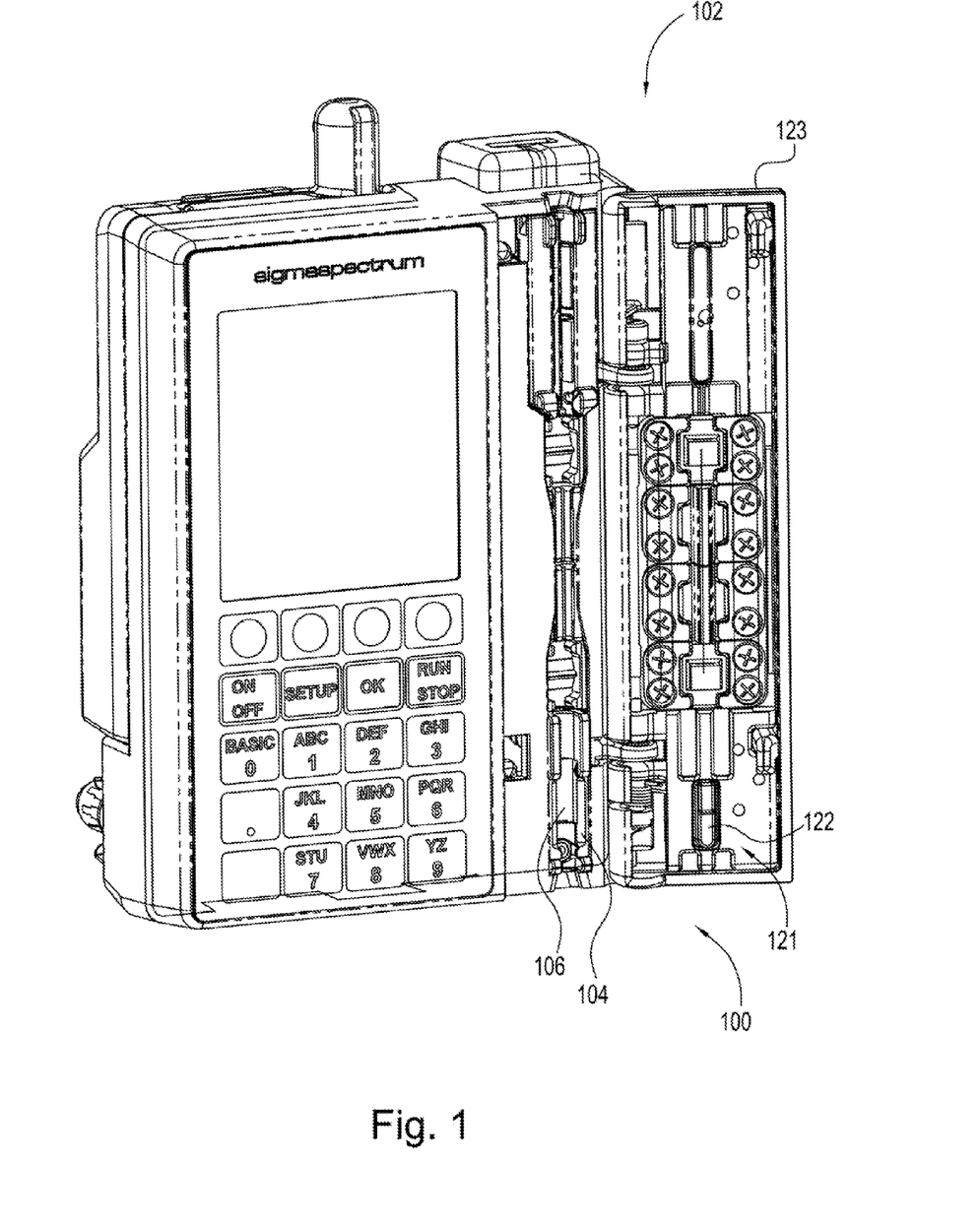
FIG. 1 is a perspective view of an infusion pump with a pressure measuring assembly.

FIG. 1 is a perspective view of an infusion pump with pressure measuring assembly 100.

Figure 2:
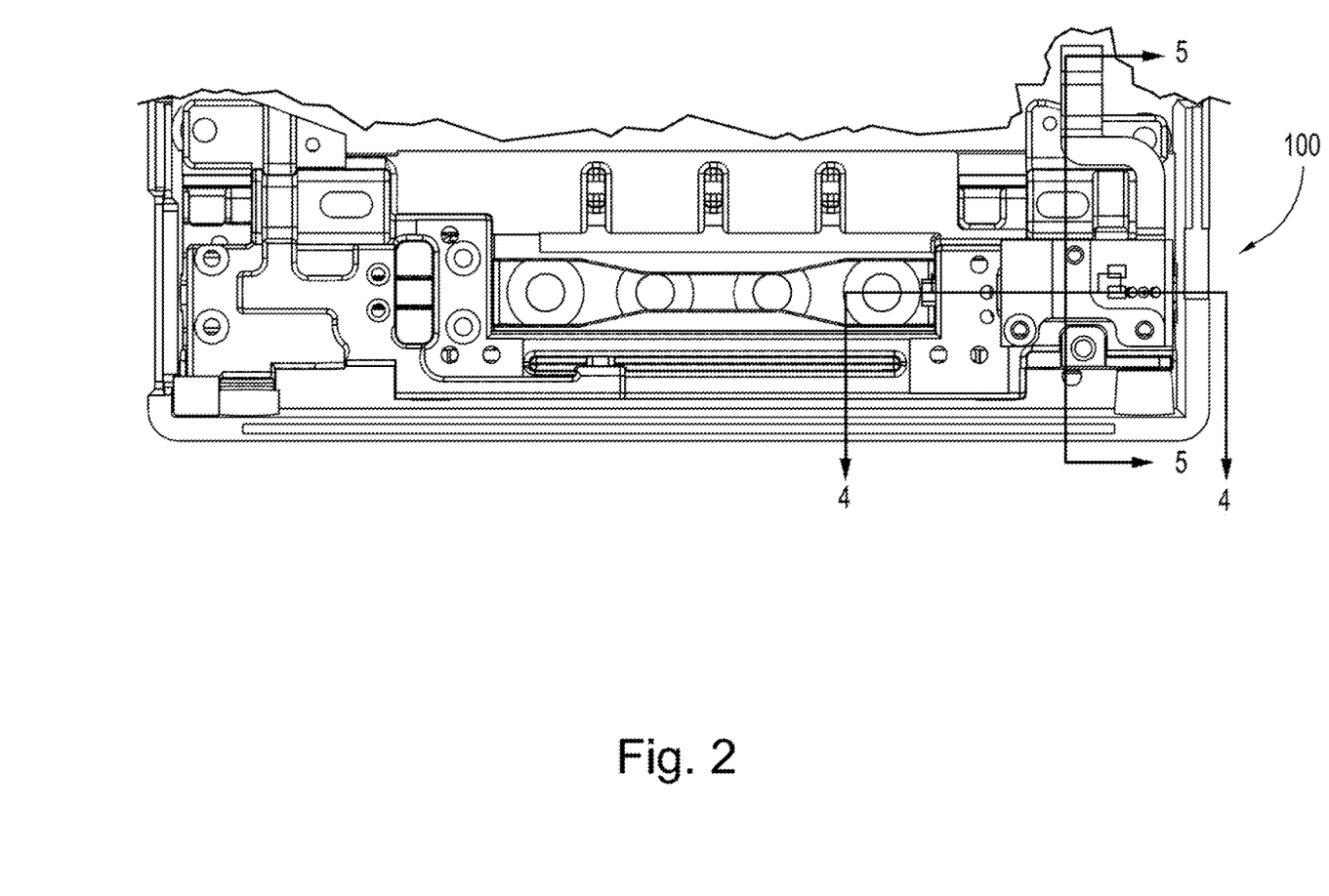
FIG. 2 is an exploded view of the pressure measuring assembly of FIG. 1.

FIG. 2 is an exploded view of pressure measuring assembly 100 of FIG. 1.

Figure 3:
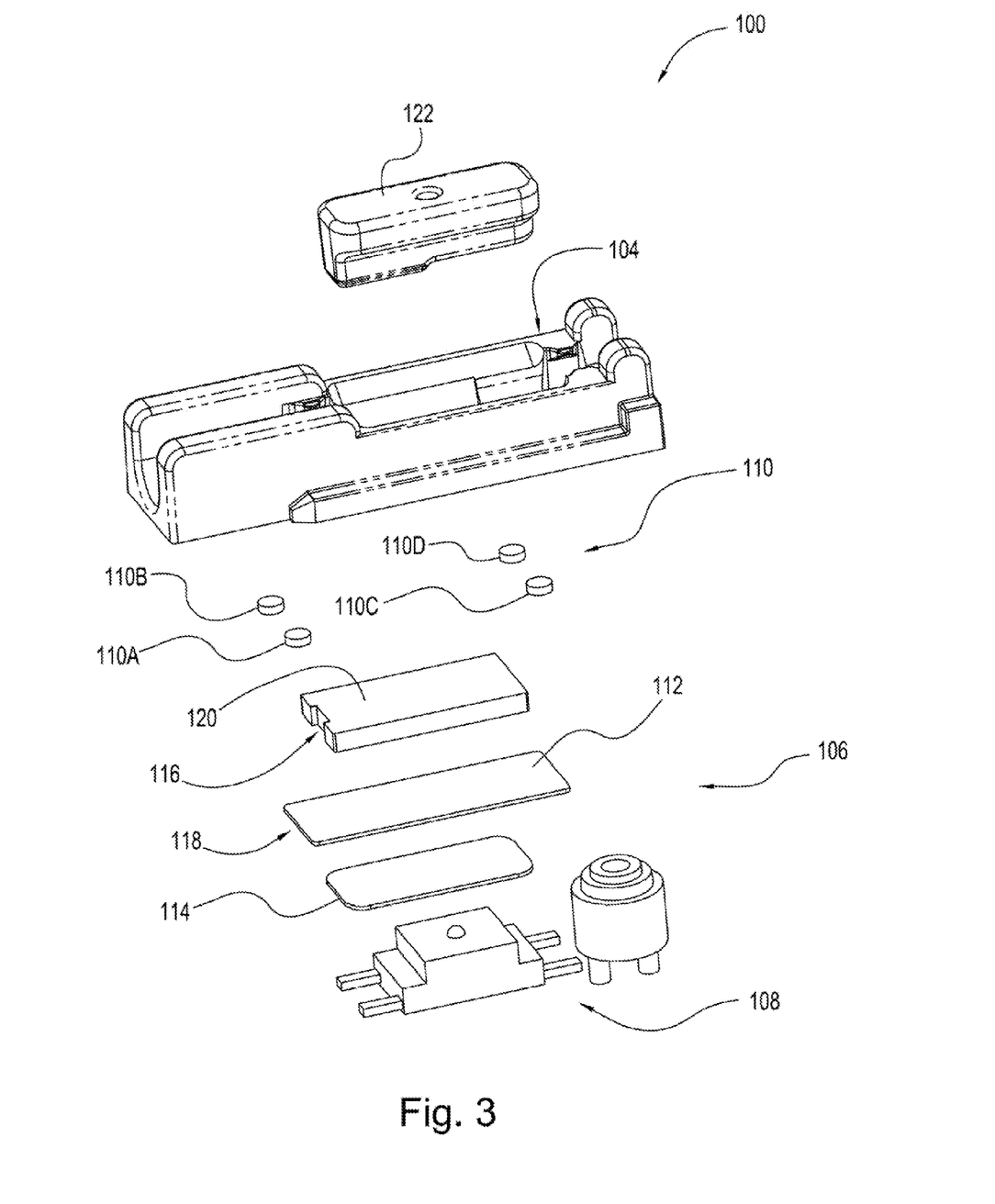
FIG. 3 is a plan view of the pressure measuring assembly of FIG. 1 with a pusher assembly in place and the cover removed.

FIG. 3 is a plan view of pressure measuring assembly 100 of FIG. 1 with a pusher assembly in place and the cover removed.

Figure 4:
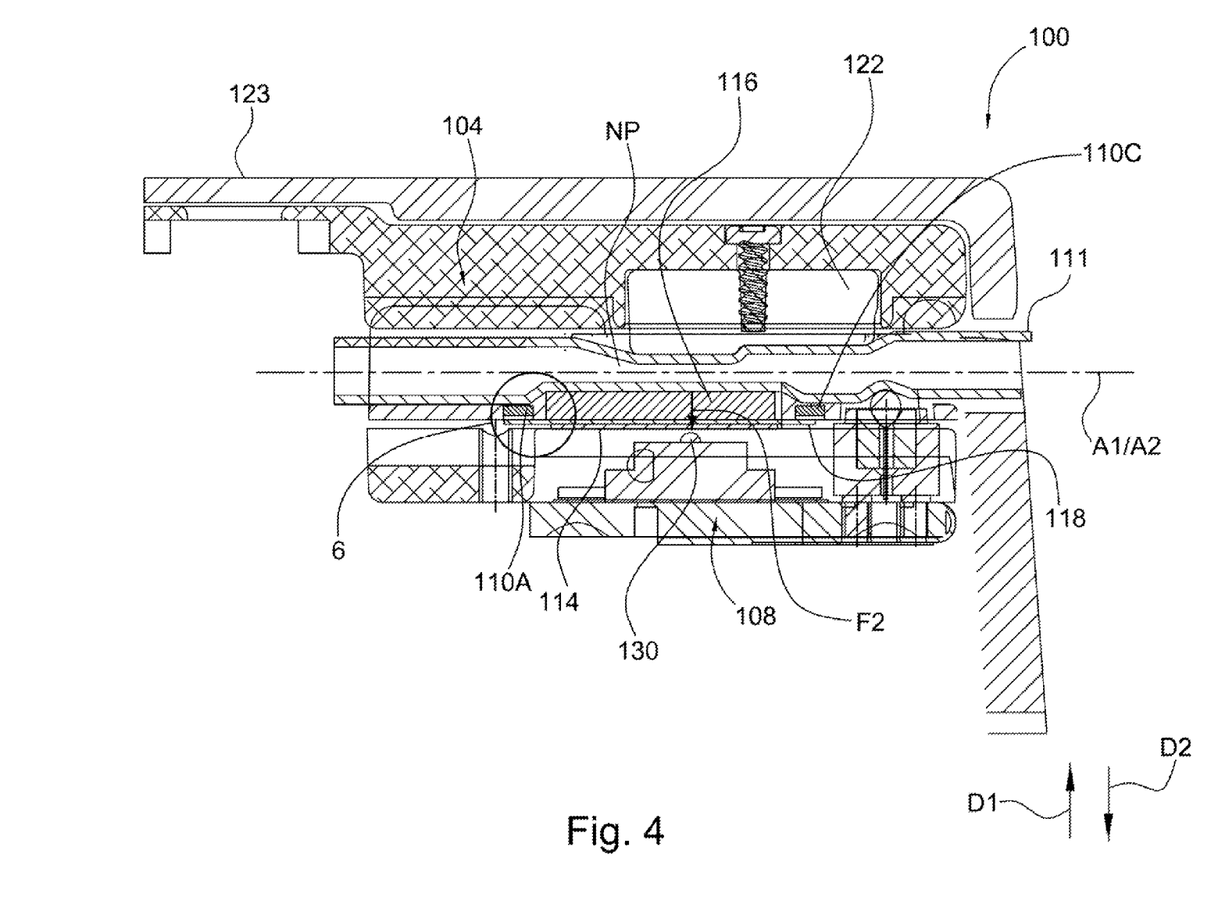
FIG. 4 is cross-sectional view generally along line 4-4 in FIG. 3 and with tubing shown.

FIG. 4 is cross-sectional view generally along line 4-4 in FIG. 3 and with tubing shown.

Figure 5:
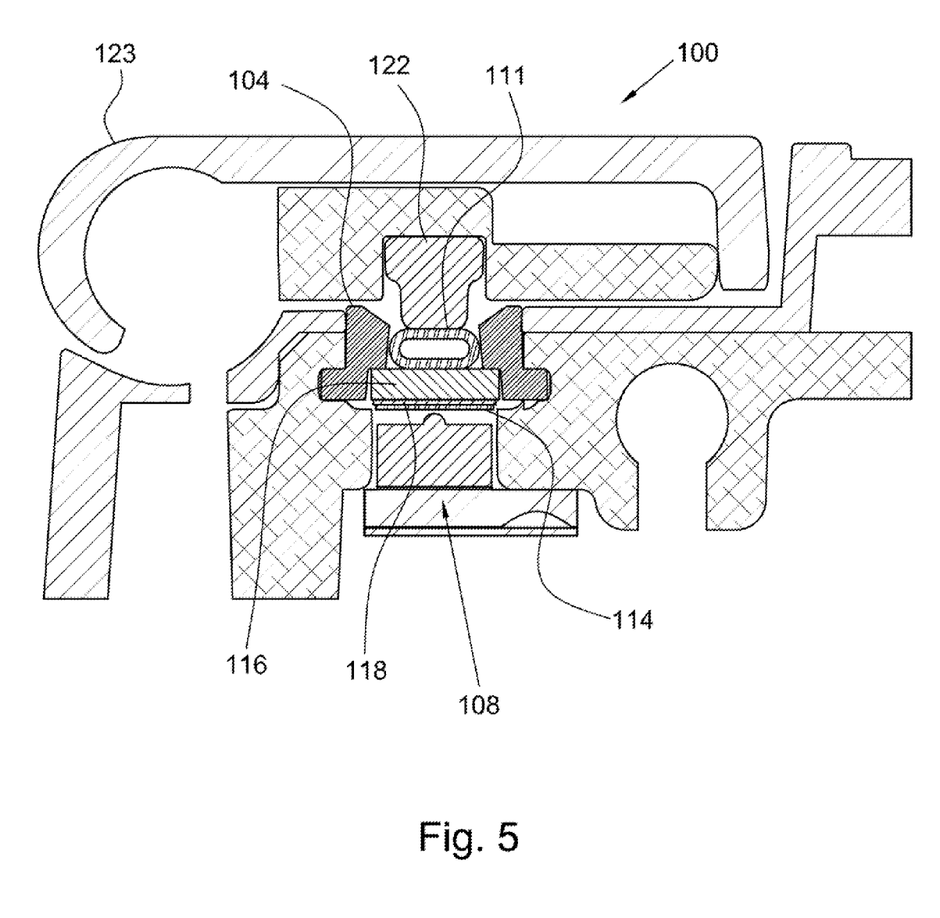
FIG. 5 is a cross-sectional view generally along line 5-5 in FIG. 3 with tubing shown and, FIG. 6 is a detail of area 6 in FIG. 4.

FIG. 5 is a cross-sectional view generally along line 5-5 in FIG. 3 with tubing shown.

Figure 6:
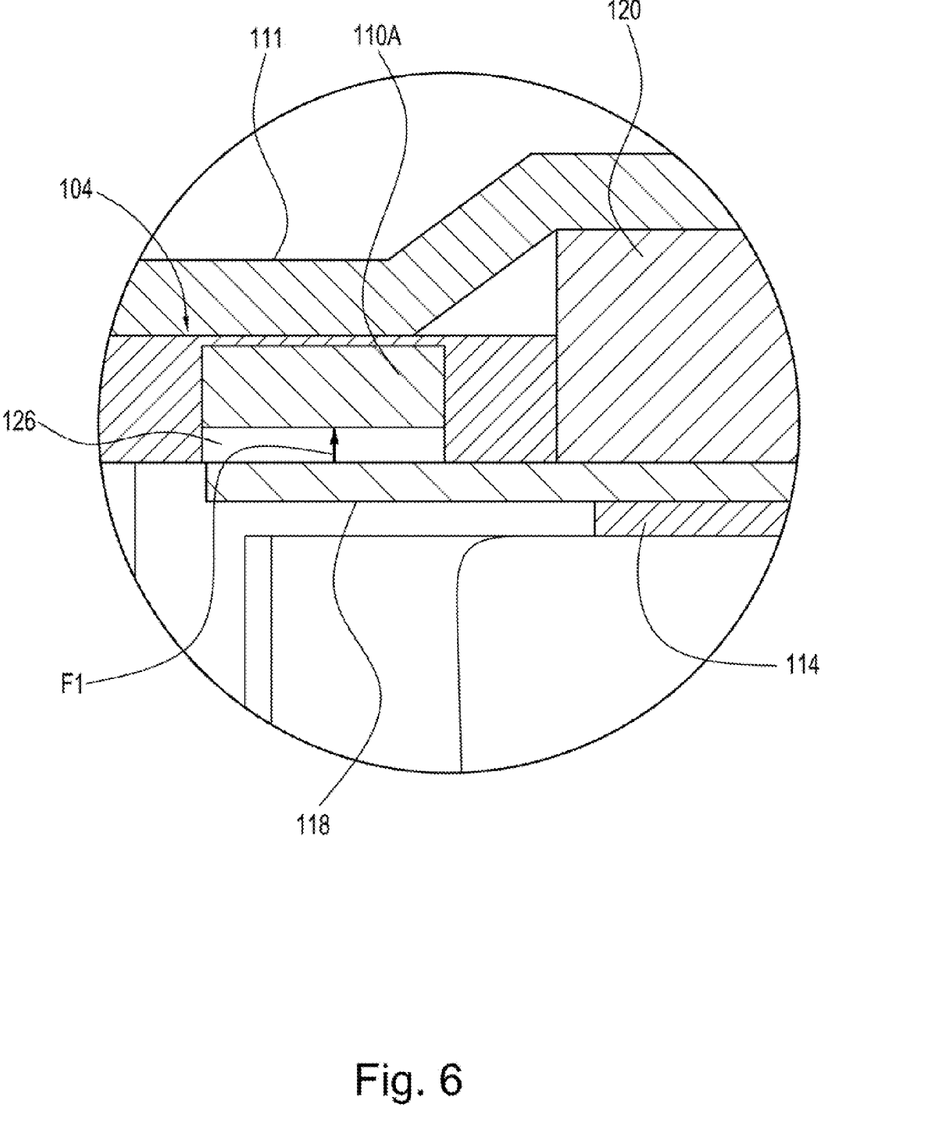

FIG. 6 is a detail of area 6 in FIG. 4. The following should be viewed in light of FIGS. 1 through 6. Pressure sensing assembly 100 for infusion pump 102 includes tubing guide 104, displaceable load assembly 106, load cell 108, and displacement assembly 110. The tubing guide is arranged to receive tubing 111 for the infusion pump. The displaceable load assembly is at least partially disposed within the tubing guide and includes at least one surface 112 facing in direction D1. The load cell faces the load assembly in direction D1. The displacement assembly is engaged with the tubing guide, faces surface 112 in direction D2, opposite the direction D1, and exerts force F1 on the load assembly in direction D1. The load cell is arranged to detect force F2, greater than the force F1, acting on the load cell in direction D2. In an example embodiment, the tubing guide includes axis A1, the tubing includes longitudinal axis A2 co-linear with A1, and D1 and D2 are orthogonal to A1/A2, for example, D1 is toward A1/A2 and D2 is away from A1/A2.

As further described below, the load assembly is displaceable in directions D1 and D2, for example in response to a load acting on the load assembly, for example, associated with compression of the tubing and pressure inside the tubing. In an example embodiment, assembly 100 includes shim 114 placed between the load assembly and the load cell. The shim is used to place a gap between the load assembly and the load cell, due to tolerance variances for example, within an acceptable range. For example, the size of gap 115 is controlled by the thickness of the shim such that the gap is large enough to prevent the shim from touching the load cell, to enable zeroing of the load cell, but is small enough to maintain desired sensitivity. That is, since displacement of the load assembly toward the load cell is proportional to the magnitude of F2, the gap is minimized such that the smallest magnitude possible for F2 causes the shim to contact the load cell. The shim is selected as needed according to any gap between the load assembly and the load cell and the particular variances in respective tolerances for component parts in assembly 100.

In an example embodiment, the load assembly includes load plate 116 and attraction plate 118 fixed to the load plate. Plate 118 includes surface 112 upon which F1 is exerted. Plate 116 includes surface 120 in contact with the tubing. Plates 116 and 118 can be made of any material known in the art and can be fixed to each other using any means known in the art. Further information regarding plates 116 and 118 is provided below.

In an example embodiment, assembly 100 includes pusher assembly 121 displaceable in direction D2 to assume a fixed position, for example, as shown in FIG. 4. In an example embodiment, assembly 121 includes pusher 122 engaged with door 123. For example, the door swivels shut to engage the pusher with the tubing. In the fixed position, assembly 122 engages the tubing and at least partially compresses the tubing. The compression of the tubing by assembly 122 results in at least a portion of force F2 operating on the load assembly. Thus, the load cell is arranged to detect force F2 in response to the disposition of the pusher assembly in the fixed position, and as further described below, a variation in force F2, for example, related to pressure within the tubing, with the pusher assembly in the fixed position.

Unlike the configuration described above, assembly 110 operates on the load assembly to attract, draw, or pull the load assembly toward the tubing guide. That is, the load assembly is pulled toward the tubing guide, rather than being pushed toward the tubing guide. Stated otherwise, the load assembly is pulled away from the load cell, rather than being pushed away from the load cell. Force F1 acts on a portion of the load assembly facing toward the tubing and tubing guide to pull the load assembly away from the load center. In contrast, in the configuration described above, a force from a resilient component acts on a portion of a load plate facing a load cell to push the load plate away from the load cell.

In an example embodiment, the displacement assembly includes a plurality of magnets 110A-110D and plate 118 is at least partially made of magnetic material. The magnets are fixed to the tubing guide and exert magnetic force F1 on the attraction plate, urging the attraction plate, and the load plate, in direction D1 away from the load cell. In the example shown, four magnets are used. In an example embodiment, rare earth magnets are used. It should be understood that other numbers, configurations, and types of magnets can be used. The magnets can be fixed to the tubing guide using any means known in the art. For example, the magnets can be placed in counter-bores 126 in surface 128 of the tubing guide such that the magnets are recessed from the surface, are even with the surface, or protrude past the surface. Thus, as long as force F1 in direction D1 from the magnets is greater than force F2 in direction D2 on the load plate, the magnets draw the attraction plate into contact with the magnets or the tubing guide (if the magnets are recessed into the tubing guide).

In an example embodiment, four (Nd—Fe—B) magnets with respective diameters of 0.0625" and respective thicknesses of 0.021" are press fit into respective bores 126 in the tubing guide. In an example embodiment, the magnets also are glued within the bores. In an example embodiment, the attraction plate is made of martensitic 17-4 PH stainless steel and is bonded or heat staked to the load plate. In an example embodiment, the shim is metallic and is fixed to the attraction plate by laser welding or other bonding.

The displacement assembly lifts the load assembly (in the absence of F2 or when greater than F2) off of the load cell, for example, holds the shim from contacting ball 130 of the load cell to enable detection of force F2. For example, when the tubing is properly positioned in the tubing guide and the pusher assembly is engaged with the tubing, the magnitude of F1 is set such that a force associated with the compression of the tubing in the proper position in the tubing guide results in F2. The detection of F2 acts as a confirmation that the tubing is properly positioned in the tubing guide. Force F2 can be a composite of the reaction of the tubing in direction D2 to the loading plate which extends in direction D1 to compress the tubing in direction D1, for example, as shown in FIG. 4, and the reaction of the tubing to the pusher assembly, which compresses the tubing in direction D2.

The displacement assembly (in the absence of F2 or when greater than F2) also holds the shim from contacting ball 130 to enable calibration and zeroing of the load cell. For example, when the tubing is removed from the tubing guide, the displacement assembly draws the load assembly off the load cell to a "no tubing" or "no load" position, which can be used as a benchmark for zeroing and calibrating. F1 also acts to prevent the load assembly from sticking in a loaded position (F2 causes the load assembly to contact the load cell). That is, after F2 causes the load assembly to engage the load cell and is then removed, F1 causes the load assembly to displace to the desired "no load" position.

In an example embodiment, assembly 100 functions as a downstream pressure monitor for the infusion pump. For example, assembly 100 can be used to detect air bubbles in fluid being infused through the tubing. Such bubbles can be dangerous for a patient receiving the fluid. In this situation, the fluid can be considered to be substantially incompressible. As fluid is being infused through the tubing with the pusher assembly in the fixed position, force F2, generated by the compression of the tubing by the pusher and load assemblies and by the presence of the infused fluid, remains relatively constant. However, if an air bubble flows through the fluid between the pusher and load assemblies, there will be a drop in F2 due to the compression of the air bubble by the fluid. For example, as the fluid passes into narrower portion NP of the tubing, the pressure on the fluid increases. Since the air bubble is compressible compared to the fluid, as the air bubble enters NP, the increase in fluid pressure surrounding the bubble compresses the bubble, reducing the pressure exerted by the fluid on the tubing walls, and thus, on the load cell. The load cell detects the pressure drop and transmits an alarm signal.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What we claim is:

1. A pressure sensing assembly for an infusion pump, comprising:
    a tubing guide arranged to receive tubing;
    a displaceable load assembly at least partially disposed within the tubing guide and with at least one first surface facing in a first direction;
    a load cell facing the load assembly in the first direction; and,
    a displacement assembly engaged with the tubing guide, facing the at least one first surface in a second direction, opposite the first direction, and exerting a first force on the load assembly in the first direction, wherein the load cell is arranged to detect a second force, greater than the first force, acting on the load cell in the second direction.

2. The pressure sensing assembly of claim 1, wherein the displacement assembly includes a plurality of magnets.

3. The pressure sensing assembly of claim 1, wherein the load assembly is displaceable in the first and second directions.

4. The pressure sensing assembly of claim 1, further comprising a shim disposed between the load assembly and the load cell.

5. The pressure sensing assembly of claim 1, wherein the displacement assembly is arranged to draw at least a portion of the load assembly toward the tubing guide.

6. The pressure sensing assembly of claim 1, wherein the load assembly includes:
    a load plate; and,
    an attraction plate fixed to the load plate, including the at least one first surface, and upon which the first force is exerted.

7. The pressure sensing assembly of claim 6, wherein:
    the displacement assembly includes a plurality of magnets; and,
    the attraction plate is magnetic.

8. The pressure sensing assembly of claim 1, further comprising a pusher assembly displaceable in the second direction to assume a fixed position facing the load assembly in the second direction, wherein:
    in the fixed position, the pusher assembly is arranged to compress the tubing; and,
    the load cell is arranged to detect:
        the second force in response to the disposition of the pusher assembly in the fixed position; and,
        a variation in the second force with the pusher assembly in the fixed position.

9. The pressure sensing assembly of claim 8, wherein the load cell is arranged to detect a variation in the second force due to a pressure variation in the tubing.

10. A pressure sensing assembly for an infusion pump, comprising:
    a tubing guide with at least one slot;
    tubing including a longitudinal axis and at least a portion disposed in the at least one slot;
    a displaceable load assembly at least partially disposed within the tubing guide and with a first surface in contact with the tubing;
    a load cell facing the longitudinal axis in a first direction; and,
    a displacement assembly facing at least a portion of the load assembly in a second direction, opposite the first direction, and exerting a first force on the load assembly in the first direction, wherein:
        in response to a second force, greater than the first force, on the first surface, the load assembly is arranged to displace in the second direction; and,
        the load cell is arranged to detect the second force.

11. The pressure sensing assembly of claim 10, wherein the load assembly includes:
    a load plate including the first surface; and,
    an attraction plate fixed to the load plate and upon which the first force is exerted.

12. The pressure sensing assembly of claim 11, wherein the displacement assembly is arranged to draw the attraction plate into contact with the tubing guide or the displacement assembly.

13. The pressure sensing assembly of claim 11, wherein:
the displacement assembly includes a plurality of magnets; and,
the attraction plate is magnetic.

14. The pressure sensing assembly of claim 10, further comprising a pusher assembly displaceable in the second direction to at least partially compress the tubing, wherein the load cell is arranged to detect:
the second force in response to the compression of the tubing by the pusher assembly; and,
a variation in the second force while the pusher assembly is at least partially compressing the tubing.

15. A pressure sensing assembly for an infusion pump, comprising:
a tubing guide arranged to receive tubing;
a displaceable load assembly at least partially disposed within the tubing guide and including:
a load plate arranged to contact the tubing; and,
an attraction plate fixed to the load plate and including a magnetic material;
a load cell; and,
a plurality of magnets, fixedly secured to the tubing guide and urging:
at least a portion of the attraction plate toward the tubing guide with a first force; and,
the load plate away from the load cell, wherein the load cell is arranged to detect a second force, greater than the first force, acting on the load plate counter to the first force.

16. A pressure sensing assembly for an infusion pump, comprising:
a tubing guide arranged to receive tubing;
a displaceable load assembly at least partially disposed within the tubing guide;
a load cell; and,
a displacement assembly engaged with the tubing guide and exerting a first force on the load assembly, wherein:
the first force draws at least a portion of the load assembly toward the tubing guide; and,
the load cell is arranged to detect a second force, greater than the first force, acting on the load assembly counter to the first force.

17. A method of measuring pressure in tubing for an infusion pump using a pressure sensing assembly including: tubing; a tubing guide; a displaceable load assembly with at least one first surface facing in a first direction; a load cell facing the load assembly in the first direction; and a displacement assembly engaged with the tubing guide, comprising:
disposing at least a portion of the tubing in the tubing guide;
exerting, using the displacement assembly, a first force on the load assembly;
drawing at least a portion of the load assembly toward the tubing guide with the first force; and,
detecting a second force, greater than the first force, acting on the load assembly counter to the first force.

18. The method of claim 1, wherein:
the load assembly includes:
a load plate; and,
a magnetic attraction plate fixed to the load plate and including the at least one first surface; and,
the displacement assembly includes a plurality of magnets, the method further comprising generating the first force with the plurality of magnets.

19. The method of claim 17, wherein the pressure sensing assembly includes a pusher assembly, the method further comprising:
displacing the pusher assembly in the second direction to assume a fixed position facing the load assembly in the second direction;
compressing the tubing with the pusher assembly; and,
detecting, using the load cell:
the second force in response to the disposition of the pusher assembly in the fixed position; and,
a variation in the second force with the pusher assembly in the fixed position.

20. A method of measuring pressure in tubing for an infusion pump using a pressure sensing assembly including: tubing; a tubing guide with at least one slot; tubing including a longitudinal axis; a displaceable load assembly; a load cell facing the longitudinal axis in a first direction; and a displacement assembly facing at least a portion of the load assembly in a second direction, opposite the first direction, the method comprising:
disposing at least a portion of the tubing in the at least one slot;
contacting a first surface of the load assembly with the tubing;
exerting, using the displacement assembly, a first force on the load assembly in the first direction;
displacing the load assembly, in response to a second force, greater than the first force, on the first surface, in the second direction; and,
detecting, using the load cell, the second force.

21. The method of claim 20, wherein:
the load assembly includes:
a load plate including the first surface; and,
a magnetic attraction plate fixed to the load plate; and,
the displacement assembly includes a plurality of magnets, the method further comprising:
generating the first force with the plurality of magnets; and,
drawing the attraction plate into contact with the tubing guide or the plurality of magnets.

22. The method of claim 20, wherein the pressure sensing assembly includes a pusher assembly, the method further comprising:
displacing the pusher assembly in the second direction;
at least partially compressing the tubing with the pusher assembly; and,
using the load cell to detect:
the second force in response to the compression of the tubing by the pusher assembly; and,
a variation in the second force while the pusher assembly is at least partially compressing the tubing.

23. A method of measuring pressure in tubing for an infusion pump using a pressure sensing assembly including: tubing; a tubing guide; a displaceable load assembly at least partially disposed within the tubing guide and including: a load plate arranged to contact the tubing and an attraction plate fixed to the load plate and including a magnetic material; a load cell; and a plurality of magnets, fixedly secured to the tubing guide, the method comprising:
disposing at least a portion of the tubing in the tubing guide;
generating a first force using the plurality of magnets;
drawing, with the first force:

at least a portion of the attraction plate toward the tubing guide; and,
the load plate away from the load cell; and,
detecting, using the load cell, a second force, greater than the first force, acting on the load plate counter to the first force.

24. A method of measuring pressure in tubing for an infusion pump using a pressure sensing assembly including: tubing; a tubing guide; a displaceable load assembly at least partially disposed within the tubing guide; a load cell; and a displacement assembly engaged with the tubing guide, the method comprising:
displacing at least a portion of the tubing in the tubing guide;
generating a first force with the displacement assembly;
drawing, using the first force, at least a portion of the load assembly toward the tubing guide; and,
detecting, using the load cell, a second force, greater than the first force, acting on the load assembly counter to the first force.

* * * * *